United States Patent [19]

Lindmark

[11] Patent Number: 5,838,811

[45] Date of Patent: *Nov. 17, 1998

[54] SYSTEM FOR MEASURING CURVED SURFACES

[76] Inventor: Richard C. Lindmark, 4712 El Hachero Ct. SE., Rio Rancho, N. Mex. 87124

[*] Notice: The term of this patent shall not extend beyond the expiration date of Pat. No. 5,539,837.

[21] Appl. No.: 799,031

[22] Filed: Feb. 10, 1997

Related U.S. Application Data

[63] Continuation of Ser. No. 590,917, Jan. 24, 1996, abandoned, which is a continuation of Ser. No. 341,841, Nov. 18, 1994, Pat. No. 5,539,837, which is a continuation-in-part of Ser. No. 875,428, Apr. 29, 1992, abandoned.

[51] Int. Cl.⁶ ........................................ G06K 9/00
[52] U.S. Cl. ............................................. 382/100
[58] Field of Search ..................... 382/100, 128, 382/199, 203, 212, 241, 242, 266, 270, 274; 356/124, 125, 127; 351/212, 219, 247

[56] References Cited

U.S. PATENT DOCUMENTS 4,685,140  8/1987  Mount, II ................................ 382/128
4,784,485  11/1988  Ho ........................................... 356/124
4,939,646  7/1990  Essinger et al. ..................... 364/413.22
5,539,837  7/1996  Lindmark ................................ 382/100

OTHER PUBLICATIONS

EyeSys™ Clinical Review, European Supplement, 3rd Quarter 1993, vol. 2, No. 3, pp. 3 and 5.
EyeSys™ Clinical Review, Published by EyeSys Technologies, Inc., 3rd Quarter 1993, vol. 2, No. 3, pp. 1, 2, 4; and sheet bearing the title "What's New From EyeSys".
"OPSM's EyeSys takes the trial and error out of fitting CLs", by Tom Padrick PhD, EyeSys Technologies, Houston, Texas, pp. 37 and 42; two sheets, one bearing the title The EyeSys™ Bottom Line For Optometry, Cost Analysis of the EyeSys Corneal Analysis System Model 3 (CAS3)™, and the second sheet title being EyeSys™ CLMA 1993.
Fundamentals of Corneal Topography, Copyright 1992, EyeSys Technologies, Inc., pp. 1–11.
"The Corneoptor™ System" Reference Manual, Scientific Advances, Inc., 1st Edition, Jul. 1968.

*Primary Examiner*—Phuoc Tran
*Attorney, Agent, or Firm*—Beck & Tysver, P.L.L.P.

[57] ABSTRACT

A transparent curved surface is illuminated and view along an orthogonal axis to generate a cross-section image of the subject surface. This image is processed to extract the first and second surfaces which are then mathematically characterized and displayed to a user.

6 Claims, 4 Drawing Sheets

FIG. 4B

POLYNOMIAL REGRESSION
$Y = A_0 * X^4 + A_1 * X^3 + A_2 * X^2 + A_3 * X + A_4$

```
A 0 =-1.995288E-04    RADIUS AT POINT  0 =  4.77    0 =  4.77
A 1 =-9.769574E-05    RADIUS AT POINT  1 =  5.02   -1 = -5.04
A 2 =-.1049047        RADIUS AT POINT  2 =  5.84   -2 = -5.86
A 3 =-2.214277E-03    RADIUS AT POINT  3 =  7.34   -3 = -7.35
A 4 = 2.335354        RADIUS AT POINT  4 =  9.68   -4 = -9.67
R^2= .9940059         RADIUS AT POINT  5 = 13.15   -5 =-13.06
                      RADIUS AT POINT  6 = 18.09   -6 =-17.87
```

| I | X | Y | Y CALC | Y CALC-Y |
|---|---|---|--------|----------|
| 1 | 4.61 | 0 | -3.986836E-03 | -3.986836E-03 |
| 2 | 4 | .5 | .5906906 | 9.069061E-02 |
| 3 | 3.39 | 1.27 | 1.092115 | -.1778846 |
| 4 | 2.5 | 1.59 | 1.664844 | 7.484376E-02 |
| 5 | 2 | 1.87 | 1.907333 | 3.733313E-02 |
| 6 | 1 | 2.21 | 2.227938 | 1.793814E-02 |
| 7 | 0 | 2.39 | 2.335354 | -5.464578E-02 |
| 8 | -4.67 | 0 | -2.711201E-02 | -2.711201E-02 |
| 9 | -4 | .59 | .62091 | 3.090996E-02 |
| 10 | -3.73 | .82 | .8505329 | .0305329 |
| 11 | -3 | 1.41 | 1.384331 | -2.566874E-02 |
| 12 | -2 | 1.94 | 1.917753 | -2.224672E-02 |
| 13 | -1.35 | 2.14 | 2.146732 | 6.732226E-03 |
| 14 | -1 | 2.21 | 2.232562 | 2.256203E-02 |

SYSTEM FOR MEASURING CURVED SURFACES

CROSS REFERENCE TO RELATED APPLICATIONS

This is a Continuation of application Ser. No. 08/590,917, filed Jan. 24, 1996, abandoned, which is a continuation of application Ser. No. 08/341,841, filed Nov. 18, 1994, U.S. Pat. No. 5,539,837, which is a continuation-in-part of Ser. No. 07/875,428, filed Apr. 29, 1992, now abandoned, applications are incorporated herein by reference.

BACKGROUND OF THE INVENTION

1. Field of the Invention

The present invention relates to apparatus for measuring transparent aspheric surfaces. Examples of such surfaces include the cornea of the eye and the surface of a contact lens. More particularly, the invention combines an optical system with a video image analysis system to generate a mathematical expression describing the shape of a transparent aspheric surface.

2. Description of the Art

In the prior art it has been recognized that accurate characterization of the shape of the surface of the cornea would aid in the fitting of contact lenses. Initially it was believed that the cornea had a substantially spheric shape and that the "fit" between the cornea and the contact lens need not be exact, for the comfort of the wearer or for operation of the lens. In general, it was believed that "soft" contact lens material would be compliant enough to conform to the corneal shape, and that only a few "base curves" would suffice to fit the majority of the population. Lindmark et al. demonstrated that the corneal shape is not spherical and that failure to accommodate the complex surface of the cornea can result in injury to the cornea itself, see "The Correction of Atypical Ametropia with Flexlens", Vol. 13, 1979, of the *Contact Lens Journal*, R. C. Lindmark, et al.

In the prior art, there have been two principal techniques used for estimating the "sphericity" of the cornea. The earliest systems involve the projection of Placido's rings onto a cornea. The practitioner observes the clarity and spacing of the projected rings and compares the resultant image pattern with reference curves to estimate which one of a collection of spherical curves most closely approximates the surface of the cornea. The earliest systems of this type relied on direct observation of the projected rings on the eye. More recent versions of this system photograph the ring pattern on the eye producing a karotograph which may be evaluated with the use of a computer system. Examples of this approach are taught by U.S. Pat. No. 4,685,140 to Mount; U.S. Pat. No. 4,978,213 to El Hage; In each of these systems a television camera is utilized along with a computer to process the Placido's ring data.

An alternate approach develops an image of the cross section image of the meridian of cornea of the eye with an optical system. This approach is typified by the Corneoptor system developed by Scientific Advances Incorporated of Columbus, Ohio in the late 1960's. This system utilizes a slit illuminator to develop a photograph of the cross section of the cornea. In use the operator would compare the photographed image with a set of test curves to determine the "best fit" representation of the contour.

It is now well recognized that the cornea of the eye has a very complex aspheric shape, and that more exact knowledge of this shape for particular individuals would be an aid to fitting contact lenses. Such a system would also be useful for evaluating the corneal surface for surgical procedures and for evaluating the base curve and front curve of contact lenses as an aid to fitting them on the human eye.

SUMMARY OF THE INVENTION

In one aspect, the present invention provides a flexible measurement tool for assessing the shape of complex aspheric transparent surfaces. For purposes of this disclosure the term "subject surface" may include any transparent surface, of which the cornea and contact lens and a contact lens on a cornea are only examples.

The apparatus of the invention includes four subsystems.

The subject surface itself is held by a positioning subsystem which preferably is a wet cell. A measurement reticle located near the subject surface may be presented along with the subject surface as an aid to calibration of the system. However it is preferred to substitute a lens with known curved surfaces into the preferred wet cell to calibrate the system.

The illumination subsystem projects a slit of light onto the subject surface along an illumination axis. An image formation subsystem is aligned along an observation axis which is orthogonal to the illumination axis. Together these two subsystems present a cross-section image of the subject surface to a camera which is associated with the image formation subsystem. The illumination subsystem and image formation subsystem can be moved with respect to the subject surface lens so that cross-sectional data sets can be taken at several positions. The camera generates a cross-sectional image of the subject surface referred to as the "raw data" This signal digitized to form a "pixel data set". The conversion process may occur within the data processing subsystem which includes a computer. Within the data processing subsystem the pixel data set is converted to a silhouette image data set. This is accomplished by an image enhancement process which applies several criteria to the pixel data set and generates a white-on-black silhouette of the particular cross section selected by the orientation of the illumination subsystem. Next Cartesian coordinates are applied to the silhouette image data set. The coordinates are applied to the silhouette image to define a first surface data set and a second surface data set. This process may involve editing the data sets to exclude non-lens areas of the subject surface. The first and second surface data sets are compared with regular conic section equations to ascertain whether they adequately represent the data sets. Assuming the conics are not suitable, the data processor computes a higher order polynomial expression for the first and second surface data sets which is displayed to the user along with an image of subject surface. Preferably a least means squares algorithm is applied to the data set to generate a polynomial expression for the curve displayed by the subject surface although a finite element analysis may be used as well.

DETAILED DESCRIPTION

Hardware Description

Figure 1:
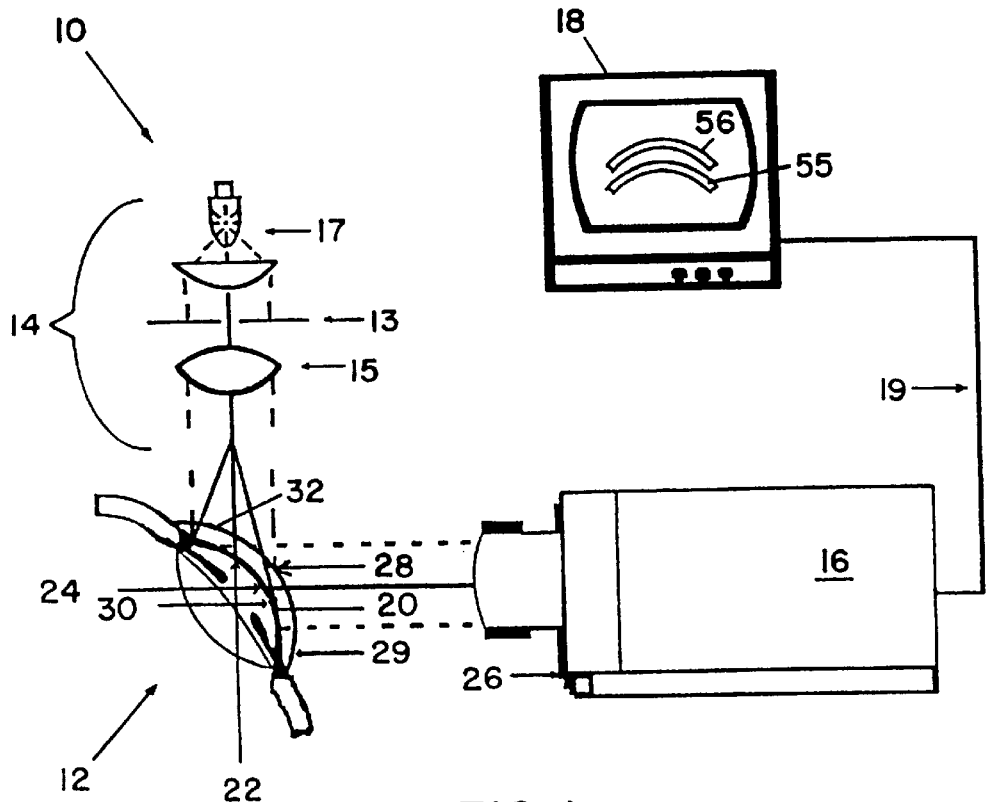
FIG. 1 is a schematic system level block diagram depicting in vivo measurement of the cornea.

The system for measuring curved surfaces 10 is shown schematically in FIG. 1. In that figure the test subject is a human eye and the positioning subsystem 12 has been placed human cornea in position along the illumination axis 22. For corneal measurements a standard head positioning assembly such as "chin rest" structure taught by the Corneopter product can be arranged to stabilize the eye position with respect to illumination subsystem 14.

The illumination subsystem 14 projects light from a light source 17 onto a slit 13. The image of the slit 13 is focused on the cornea by a lens 15. This optical train defines the illumination axis 22. It should be appreciated that a laser could also be used to scan the cornea as an alternative to the incandescent filament and slit system-depicted in FIG. 1 and FIG. 2.

The image forming subsystem 16 is provided to view the first surface 28 and the second surface 30 of the cornea 20 along an observation axis 24 that is orthogonal to the illumination axis 22. The user can adjust the relative orientation of the illumination axis 22 and the observation axis 24 to the eye to realize a good image. The user may rotate the entire optical subassembly about the illumination axis 22 to several positions to fully characterize the cornea. The image forming subsystem 16 includes a CCD or CID or other type of imaging device 26 which is used to generate an image of the cross section of the cornea 20. The RCA model CC285 camcorder is one suitable device for carrying out the invention.

A reticle 29 may be positioned on the same plane as the image of the cornea 20 to facilitate system calibration. It is preferred to introduce a contact lens having a known curve into a wet cell and use this reference lens for calibration. It is desirable to use a lens that rides on the sclera of the eye so that the surface of the lens does not "ride" on the surface of the cornea.

Typically the camera or imaging device 26 will transmit an analog video signal of the subject surface and reticle, if present, to the data processor subsystem 18. IBM 286 AT class computers or better may be used for carrying out the invention. The data processor subsystem 18 will include an appropriate analog to digital converter or a frame grabber utility to capture a camera image. A suitable PC compatible board for carrying out these functions is the Supervision PC Image Capture Board available from IDEC, Inc. of Fountainville, Pa. Alternative boards are available as well including the Epix and Matrox "video frame grabber" products. It is preferred to have a minimum resolution of 512×400 pixels, and higher resolution is desirable.

The data processor subsystem 18 processes this video data to calculate and display a mathematical expression characterizing the first surface 28 and second surface 30 of the cornea 20.

Figure 2:
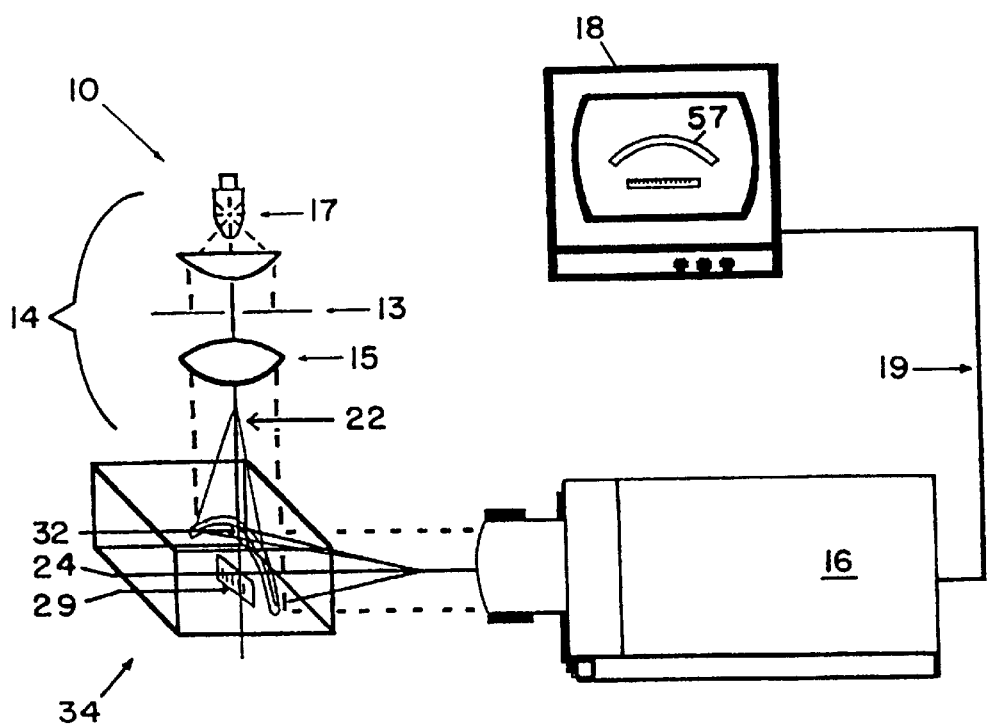
FIG. 2 is a schematic system level block diagram depicting wet cell measurement of a hydrated contact lens.

In FIG. 2 the lens positioning subsystem 12 includes a wet cell 34 which stabilizes and positions the contact lens 32 along the illumination axis 22. The wet cell 34 will contain an equilibriating saline solution to hydrate or stabilize the shape of contact lens 32. Detail cell design must ensure that the structure is properly viewed and is free of adherent air bubbles. The viscosity, index of refraction and density of the wet cell support fluid may be adjusted to improve imaging. In general a mixture of methyl cellulose and water may be formed to support the lens at neutral buoyancy. At neutral buoyancy the lens is stress free and the shape is uninfluenced by contact with the cell. The Hydrocurve wet cell formerly manufactured by Soft Lenses, Inc of San Diego, represents one type of suitable design. This product formed a lens chamber from plexiglas with side walls of glass. The remainder of the physical system is similar to the system used for taking measurements from the cornea. However, certain software routines may differ between in vivo corneal measurements and wet cell measurements.

When a contact lens 32 is placed on a patient, the physiologic system of the eye serves to bathe the contact lens 32 with tears which also act as an equilibrating solution and meets the requirement set forth for a wet cell.

Data Processing Description

Figure 3:
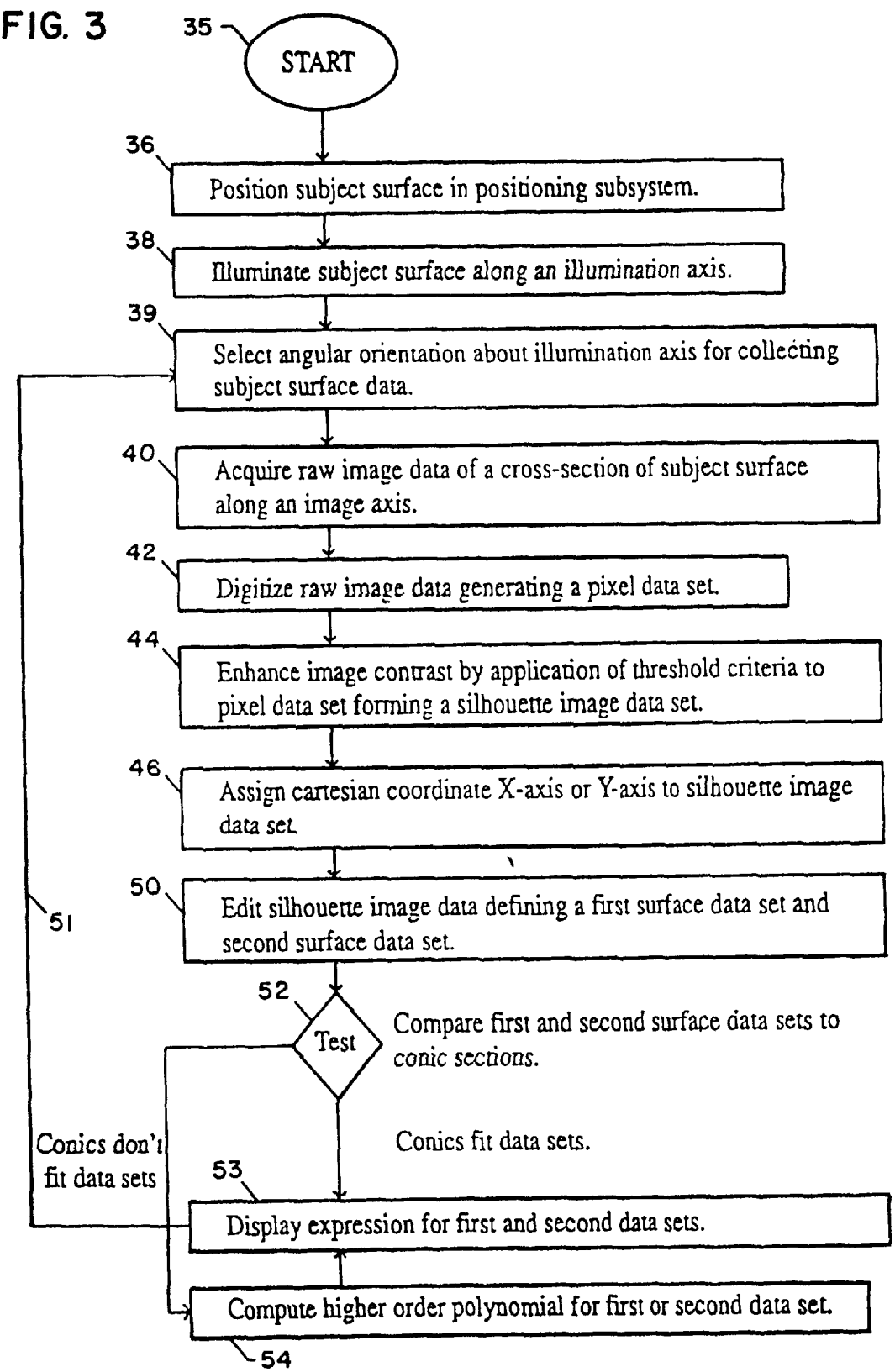
FIG. 3 is a system level flowchart for the measurement process.

FIG. 3 sets forth the system level flowchart for the software processes used to carry out the invention. Several commercially available "off-the-self" software products can be used to execute the steps of the process. Catenary Systems Victor Imaging Processing Library, Auto Desk AutoCad, Generic Cadd, Zsoft Corporation PC Paintbrush IV Plus, are suitable PC products which have been used to prototype the invention. However, incompatible file formats between software products renders this approach cumbersome and custom software code should be developed to facilitate use of the system.

The process begins at start process block 35. Process block 36 is entered and the test specimen or subject surface is positioned. In process block 38 the subject surface is illuminated along the illumination axis 22. For each angular position about the illumination axis, a unique cross-section of the subject surface is illuminated and evaluated. Typically, the amount of illumination will be in a user adjustable parameter, which can be optimize to ensure adequate illumination intensity to generate an adequate gray scale image of the test surface. In process block 39, the camera and illumination subsystem 14 may be rotated about the illumination axis 22 so that additional cross-sections of the test surface may be acquired. Typically, at least two separate cross-section images will be developed, although a larger number may be required to accurately characterize a complex shape. In process block 40, a raw image is acquired of the cross-section of the subject surfaces along the orthogonal observation axis 24. Although any of a variety of camera systems can be used to acquire the image, the preferred structure is a video camera generating an analog video output for delivery via connection 19 to a computer or data processor subsystem 18. In process block 42, the analog cross-sectional image is converted to a pixel data set. This conversion process requires the analog-to-digital conversion of the video image, and conventional image capture hardware can be utilized within the data processor subsystem 18 to achieve this result. Turning to process block 44, the gray scale image of the subject surface is converted from gray scale to black and white scale pixels generating the silhouette image of the transparent portion of the test surface. This process is achieved by establishing a gray scale threshold, and assigning black pixels to values below the threshold, and white pixels to values above the threshold. This procedure generates the silhouette, and will exclude opaque structures from the composite image. This preferred technique sets non-selected pixel values to zero which are then excluded from the lens data set. This technique effectively reduces the size of the image file which is an aid to further analysis. For example the small image file can be tested for the presence of contiguous data points which presumably lie on the lens surface. Non-contiguous points may be excluded thus removing non image pixels which have the same pixel density as lens data pixels. It is also possible to test the reduced image set collect the data pixels into two separate sets representing the front surface and the rear surface of the lens. This extraction and manipulation process may be performed automatically without operator intervention and is generally referred to herein as "contrast enhancement".

In the case of the human cornea, this contrast enhancement structure may generate silhouettes of internal structures of the eye which are not of interest in characterizing the shape of the cornea. The internal structure may be enhanced to better examine corneal anatomy or pathological conditions, and this data recorded for future comparison and use. With the silhouette image generated, file conversion utilities may be used to convert the silhouette image data set to a computer automated design program (CAD). The CAD software permits overlaying cartesian coordinates on the image in process block 46. Typically such software permits the user to edit the image to eliminate limbus points, and other portions of the image which do not need to be characterized. This step of the process is depicted as process block 50. The CAD software is utilized to collect a set of "X", "Y" cartesian coordinates for the anterior transparent surface of the cornea referred to as the first surface data set, as well as for the posterior surface, referred to as the second surface data set. This is depicted in FIG. 2 by curve trace 57. When a calibration lens is used an additional third anterior surface data set and a fourth posterior data set information must be collected as seen from the lens surfaces represented by trace 55 and trace 56 on FIG. 1. Through suitable conversion utilities, these coordinates can be delivered to mathematical modeling software such as the "Mathematica" product published by Wolfram Research. The mathematical function software is applied to the reduced data sets in process block 52 and is used to compare the coordinate sets with regular conic sections. For some surfaces, for example, contact lenses conic section data may adequately represent the surface contour, and the computational overhead required for this comparison is relatively low. This testing procedure, may generate an output to be displayed to the user as represented by process block 53, if the conic curves adequately represent the data set information. If the subject surface is very irregular, the mathematical software in process block 54 can be used to compute a higher order polynomial expression for the first surface and second surface curves. Upon completion of this curve fitting routine, the polynomial expressions can be displayed for the user in process block 53. This process is repeated via transition 51 for each of the cross-sections which returns data flow for additional cross-sections of the subject surface. This process step may include manually reorienting the observation and illumination structures to different positions.

Figure 4A:
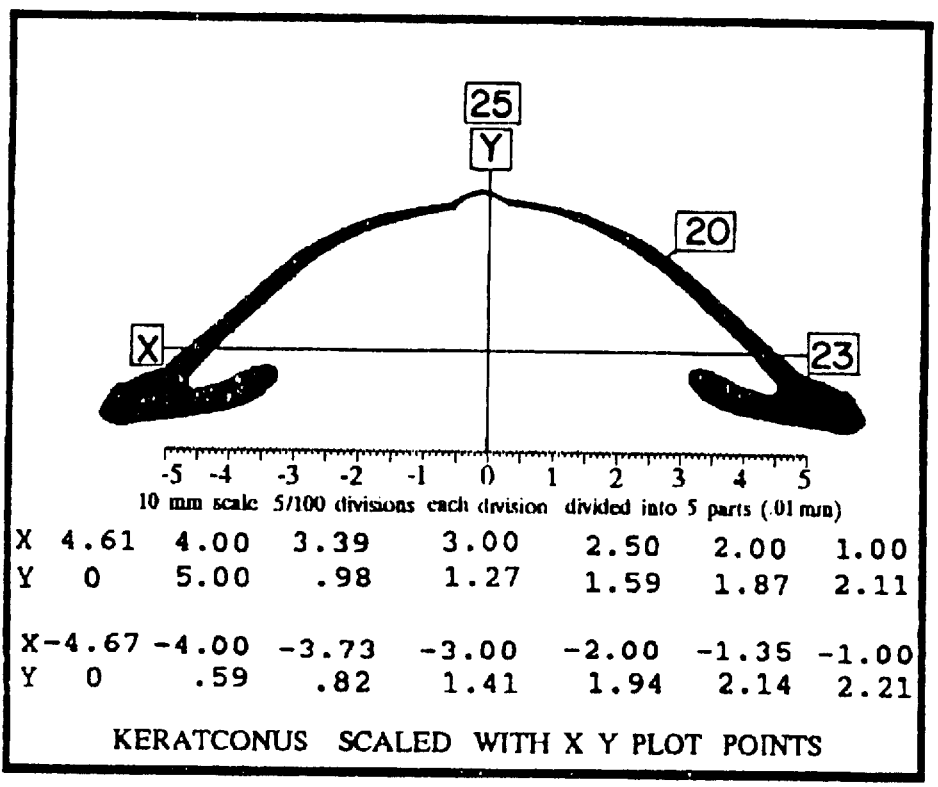
FIG. 4 is schematic diagram depicting the process of evaluating a corneal shape, and depicting a display of the calculated data.

FIG. 4 represents schematic applications of the algorithm to images captured by the camera. In FIG. 4, the black on white silhouette of the cornea 21 has been digitized and imported into CAD software where the cartesian coordinates 23 and 25 have been manually positioned to exclude non-lens features of the image. The CAD system has been used to find the midpoint of the X axis, which is defined as the Y axis coordinate. The reduced data sets drawn from the CAD program are imported to the mathematical processes set forth on FIG. 3, resulting in the computation of the polynomial expression for the anterior and posterior surfaces.

Although the invention has been described in connection with an illustrative embodiment, it should be understood that the teaching is illustrative and that various changes can be made without departing from the scope of the invention.

What is claimed is:

1. Apparatus for measuring a transparent curved subject surface and for presenting a mathematical expression describing the curvature of said transparent curved subject surface to a user and displaying an image of the subject surface to a user comprising:

an illumination subsystem for directing light along an illumination axis;

an image formation subsystem for acquiring image data, along an observation axis at an angle to said illumination axis;

a positioning subsystem for locating and positioning said transparent curved subject surface proximate the intersection of observation axis and said illumination axis;

data processor subsystem coupled to said image formation subsystem for accepting said image data and for converting said image data into an image pixel data set;

contrast enhancement means for generating a silhouette image data set of said curved surface from said image pixel data set;

coordinate assigning means for defining a set of coordinates to said silhouette data set;

curve approximating means for defining a mathematical expression for said silhouette data set;

display means for displaying said image pixel data set and said mathematical expression to a user.

2. The apparatus of claim 1 wherein said positioning subsystem further comprises rotation means for rotating said image formation subsystem and said illumination subsystem together about a third axis perpendicular to the plane defined by said illumination axis and said observation axis whereby said image formation subsystem collects a plurality of image data sets.

3. A method of measuring a transparent curved subject surface and displaying data to a user comprising the sequential steps of:

positioning said subject surface along an illumination axis;

illuminating said subject surface along said illumination axis;

selecting an angular location about said illumination axis for collecting data;

acquiring raw image data of the cross-section of said subject surface, said image defining said raw data;

digitizing said raw image data to define a set of pixel data;

enhancing the contrast of said pixel data producing a silhouette image data set;

assigning coordinates to said silhouette data set;

computing a mathematical expression for said silhouette data set;

displaying said pixel data to a user as an image;

displaying said mathematical expression and said silhouette image to a user.

4. The method of claim 3 wherein said enhancing step includes:

establishing a pixel data threshold;

setting pixel data below said pixel threshold to zero;

retaining as said silhouette data set the pixel having a non-zero value;

comparing pixels in said silhouette data set with each other and dividing said silhouette data into an array of front surface data and an array of rear surface silhouette data.

5. Apparatus for measuring a transparent curved subject surface and for presenting a mathematical expression describing the curvature of said transparent curved subject surface to a user comprising:

an illumination subsystem for directing light along an illumination axis;

an image formation subsystem for acquiring image data, along an observation axis orthogonal to said illumination axis;

a positioning subsystem for locating and positioning said transparent curved subject surface proximate the intersection of observation axis and said illumination axis;

data processor subsystem coupled to said image formation subsystem for accepting said image data and for converting said image data into a pixel data set;

contrast enhancement means for generating a silhouette image data set of said curved surface from said pixel data set;

coordinate assigning means for defining a set of coordinates to said silhouette data set;

curve approximating means for defining a mathematical expression for said silhouette data set;

display means for displaying said silhouette data set and said mathematical expression to a user.

6. The apparatus of claim 1 wherein said positioning subsystem further comprises rotation means for rotating said image formation subsystem and said illumination subsystem together about a third axis perpendicular to the plane defined by said illumination axis and said observation axis whereby said image formation subsystem collects a plurality of image data sets, each of said image data sets being taken in a direction orthogonal to said illuminating axis.

* * * * *